United States Patent [19]

Hansen et al.

[11] Patent Number: 5,104,979
[45] Date of Patent: Apr. 14, 1992

[54] POLYAZO DYES WITH DIAZO COMPONENTS OF THE AMINOPHENOL AND THE AMINO DIPHENYL-SULFIDE, -SULFOXIDE OR -SULFONE SERIES

[75] Inventors: Guenter Hansen, Ludwigshafen; Georg Zeidler, Dannstadt-Schauernheim; Ortwin Schaffer, Ludwigshafen, all of Fed. Rep. of Germany

[73] Assignee: BASF Aktiengesellschaft, Ludwigshafen, Fed. Rep. of Germany

[21] Appl. No.: 559,996

[22] Filed: Jul. 31, 1990

Related U.S. Application Data

[63] Continuation of Ser. No. 389,799, Aug. 4, 1989, abandoned.

[30] Foreign Application Priority Data

Aug. 12, 1988 [DE] Fed. Rep. of Germany ....... 3827447

[51] Int. Cl.$^5$ .................. C09B 45/32; C09B 33/044; C09B 33/08; C09B 33/24; D06P 1/10
[52] U.S. Cl. .................... 534/677; 534/678; 534/680; 534/682; 534/683; 534/684; 534/685; 534/688
[58] Field of Search ............... 534/677, 678, 680–685, 534/688

[56] References Cited

U.S. PATENT DOCUMENTS

| | | | |
|---|---|---|---|
| 1,805,715 | 5/1931 | Brightman | 534/677 |
| 2,045,090 | 6/1936 | Lange et al. | 534/680 |
| 2,183,673 | 12/1939 | Dobler et al. | 534/688 X |
| 2,204,230 | 6/1940 | Rossander et al. | 534/678 |
| 2,438,754 | 3/1948 | Krebser et al. | 534/688 X |
| 3,406,160 | 10/1968 | Wicki | 534/688 X |
| 3,787,387 | 1/1974 | Wicki | 534/688 X |
| 3,965,087 | 6/1976 | Konishi et al. | 534/680 |
| 3,975,369 | 8/1976 | Wicki | 534/688 X |
| 4,263,229 | 4/1981 | Studer et al. | 534/688 X |
| 4,424,152 | 1/1984 | Mennicke et al. | 534/688 X |
| 4,587,292 | 5/1986 | Doswald et al. | 534/688 X |

FOREIGN PATENT DOCUMENTS 191126 8/1986 European Pat. Off. ............ 534/688
3263 of 1891 United Kingdom ................ 534/688

OTHER PUBLICATIONS

El-Ezbawy et al, Chemical Abstracts, vol. 113, No. 78227a (1990).

*Primary Examiner*—Robert W. Ramsuer
*Assistant Examiner*—Fiona T. Powers
*Attorney, Agent, or Firm*—Oblon, Spivak, McClelland, Maier & Neustadt

[57] ABSTRACT

Polyazo dyes useful for dyeing leather in the free form or as copper, chromium, iron, cobalt or nickel complexes have the formula

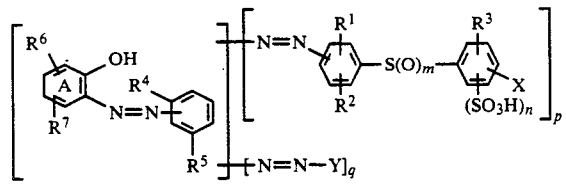

where m is 0, 1 or 2, n is 0 or 1, p is from 1 to 2, q is from 0 to 1, and $R^1$, $R^2$, $R^3$, $R^4$, $R^5$, $R^6$, $R^7$, X, Y and the ring A are each as defined, and may be prepared from aniline derivatives of the formula

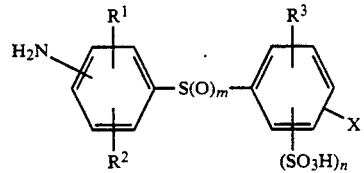

where m is 0, 1, or 2, n is 0 or 1, and X, $R^1$, $R_2$ and $R^3$ are each as defined.

2 Claims, No Drawings

POLYAZO DYES WITH DIAZO COMPONENTS OF THE AMINOPHENOL AND THE AMINO DIPHENYL-SULFIDE, -SULFOXIDE OR -SULFONE SERIES

This application is a continuation of application Ser. No. 07/389,799, filed on Aug. 4, 1989, now abandoned.

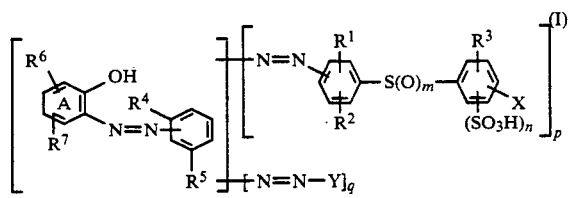

where
ms is 0, 1 or 2,
n is 0 or 1,
p is from 1 to 2,
q is from 0 to 1,
X is hydrogen or nitro,
$R^1$ and $R^2$ are identical or different and each is independently of the other hydrogen, $C_1$-$C_4$-alkyl, $C_1$-$C_4$-alkoxy, halogen or hydroxysulfonyl,
$R^3$ is hydrogen, $C_1$-$C_4$-alkoxy, halogen, carboxyl, nitro or $C_1$-$C_4$-alkanoylamino,
$R^4$ and $R^5$ are identical or different and each is independently of the other hydroxyl or amino,
$R^6$ is hydrogen, $C_1$-$C_4$-alkyl, halogen, nitro, hydroxy-sulfonyl, sulfamoyl, $C_1$-$C_4$-monoalkylsulfamoyl, C or $C_1$-$C_4$-alkylsulfonyl,
$R^7$ is hydrogen, halogen, nitro or hydroxysulfonyl and
Y is a radical of the formula

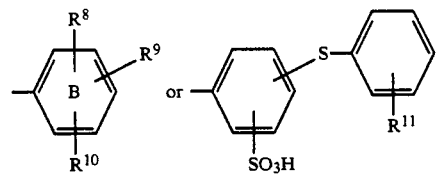

where
$R^8$ is hydrogen, hydroxyl, halogen, nitro or hydroxysulfonyl,
$R^9$ is hydrogen, halogen, nitro or hydroxysulfonyl,
$R^{10}$ is hydrogen, $C_1$-$C_4$-alkyl, $C_1$-$C_4$-alkoxy or hydroxy-sulfonyl and
$R^{11}$ is hydrogen, $C_1$-$C_4$-alkyl, $C_1$-$C_4$-alkoxy, halogen or carboxyl, and the
rings A and B may each be fused with an unsubstituted or nitro- or hydroxysulfonyl-substituted benzo ring, in the free form or as a copper, chromium, iron, cobalt or nickel complex, and to intermediates therefor.

CH-A-571,599, DE-A-2,024,047, DE-A-2,162,419 and EP-A-45,868 describe polyazo dyes which are similar to those of the formula I. However, instead of the $-S(O)_m-$ linkage they have an amino linkage.

It is an object of the present invention to provide novel polyazo dyes which should be easily accessible and have advantageous application properties.

We have found that this object is achieved by the dyes of the above formula I.

All the alkyl groups appearing in the compounds according to the invention can be not only straight-chain but also branched.

$R^1$, $R^2$, $R^3$, $R^{10}$ and $R^{11}$ are each for example methoxy, ethoxy, propoxy, isopropoxy, butoxy, isobutoxy or sec-butoxy.

$R^1$, $R^2$, $R^{10}$ and $R^{11}$ are each further for example, like $R^6$, methyl, ethyl, propyl, isopropyl, butyl, isobutyl or sec-butyl.

$R^1$, $R^2$, $R^3$, $R^6$ and $R^{11}$ are each further for example (like $R^7$, $R^8$ and $R^9$) fluorine, chlorine or bromine, the preferred halogens being chlorine and bromine.

$R^3$ is further for example formylamino, acetylamino, propionylamino, butyrylamino or isobutyrylamino.

$R^6$ is further for example monomethylsulfamoyl, dimethylsulfamoyl, monoethylsulfamoyl, diethylsulfamoyl, monopropylsulfamoyl, dipropylsulfamoyl, monoisopropylsulfamoyl, diisopropylsulfamoyl, monobutylsulfamoyl, dibutylsulfamoyl, methylsufonyl, ethylsulfonyl, propylsulfonyl, isopropylsulfonyl or butylsulfonyl.

The indices p and q can each also be fractions of whole numbers, in which case mixtures of polyazo dyes are present.

It will be readily understood that if the polyazo dyes of the formula I contain one or more hydroxysulfonyl groups the salts thereof also come within the scope of the present invention.

These salts can be metal or ammonium salts. Metal salts are in particular the lithium, sodium or potassium salts. Ammonium salts for the purposes of the present invention are those salts which have either unsubstituted or substituted ammonium cations. Substituted ammonium cations are for example monoalkyl-, dialkyl-, trialkyl-, tetraalkyl- or benzytrialkyl-ammonium cations or those cations which are derived from nitrogenous five- or six-membered saturated heterocycles, such as pyrrolidinium, piperidinium, morpholinium, piperazinium or N-alkyl-piperazinium cations or N-monoalkyl- or N,N-dialkyl-substituted products thereof. Alkyl here is to be understood as meaning in general straight-chain or branched $C_1$-$C_{20}$-alkyl which may be substituted by hdyroxyl groups and/or interrupted by oxygen atoms.

Preference is given to polyazo dyes of the formula Ia

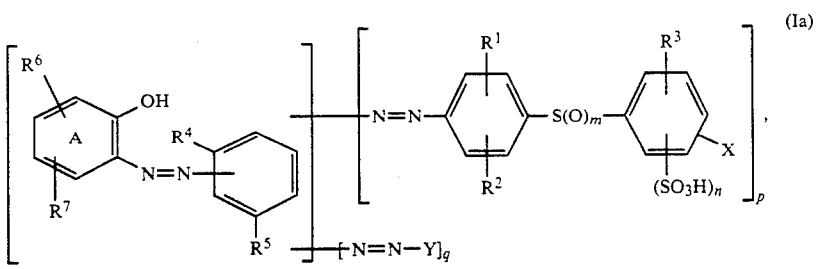

where $R^3$ is hydrogen and $R^1$, $R^2$, $R^4$, $R^5$, $R^6$, $R^7$, X, Y, m, n, p, q and the ring A are each as defined above.

Preference is further given to polyazo dyes of the formula I where m is 0 or 2, q is 0, X is nitro, $R^1$ and $R^2$ are each hydrogen and $R^3$ is hydrogen or nitro.

Particular preference is given to such polyazo dyes of the formula I where m is 0.

If $R^3$ is hydrogen, X is nitro and n is 1, preference is given in particular to those dyes of the formula I where the nitro group (X) is ortho and the hydroxysulfonyl group para to the $-S(O)_m-$ linkage or the nitro group (X) is para and the hydroxysulfonyl group ortho to the $-S(O)_m-$ linkage.

Preference is further given to the copper, chromium, iron or cobalt complexes of the polyazo dyes of the formula I, of which the corresponding iron or chromium complexes must be mentioned in particular.

The polyazo dyes according to the invention can be obtained in a conventional manner.

For example, an aminophenol of the formula III

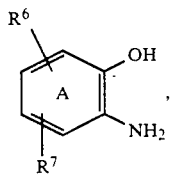

where $R^6$ and $R^7$ and the ring A are each as defined above, can be diazotized and coupled with a coupling component of the formula IV

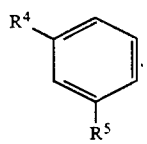

where $R^4$ and $R^5$ are each as defined above, forming a monoazo compound of the formula V

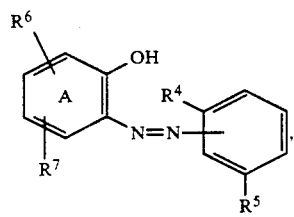

where $R^4$, $R^5$, $R^6$, $R^7$ and the ring A are each as defined above.

Thereafter an aniline derivative of the formula

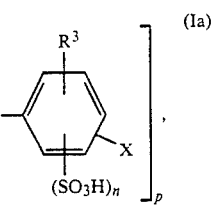

where $R^1$, $R^2$, $R^3$, X, m and n are each as defined above, can be diazotized and coupled with the above-described monoazo compound V.

If desired, an amine of the formula VI $$Y-NH_2 \quad (VI),$$

where Y is as defined above, can then be diazotized and coupled with the diazo dye of the formula I (where q=0).

This example of a method of preparation need not of course be adhered to; that is, it is also possible to vary the coupling sequence. For instance, first the aniline derivative II can be diazotized and coupled with the coupling component IV and the resulting reaction product can then be coupled with a previously diazotized aminophenol III.

The metallization, ie. the preparation of the respective copper, chromium, iron, cobalt or nickel complexes of the polyazo dyes I, is likewise effected in a conventional manner, for example by treating the polyazo dye with the corresponding metal salts, for example with iron(III) chloride, iron(II) sulfate, copper sulfate or chromium(III) formate, in aqueous solution at from 80° to 105° C. and at pH 4-6.

The aminophenols III and the coupling component IV are compounds known per se.

The present invention further provides aniline derivatives of the formula II

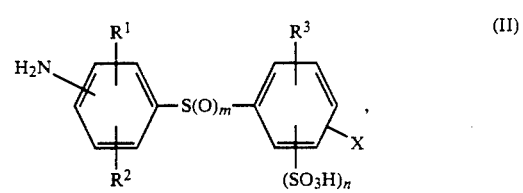

where
m is 0, 1 or 2,
n is 0 or 1,
X is hydrogen or nitro,
$R^1$ and $R^2$ are identical or different and each is independently of the other hydrogen, $C_1$–$C_4$-alkyl, $C_1$–$C_4$-alkoxy, halogen or hydroxysulfonyl, and $R^3$ is hydrogen, $C_1$-$C_4$-alkoxy, halogen, carboxyl, nitro or $C_1$-$C_4$-alkanoylamino.

For examples of the radical $R^1$, $R^2$ and $R^3$, see the lists given above.

The novel aniline derivatives of the formula II, which are useful diazo components for preparing polyazo dyes of the formula I or indeed other azo dyes, can be obtained in a conventional manner.

For example, a nitro compound of the formula VII

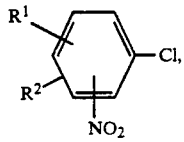
(VII)

where $R^1$ and $R^2$ are each as defined above, can be reacted with an alkali metal sulfide to give a thiophenol derivative VIII

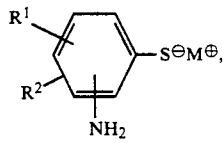
(VIII)

where $M^\oplus$ is an alkali metal cation and $R^1$ and $R^2$ are each as defined above.

This thiophenol derivative VIII produces by reaction with the chlorobenzene derivative of the formula IX

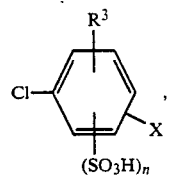
(IX)

where $R^3$, X and n are each as defined above, the novel aniline derivative of the formula II (where m=0). By oxidization of these thio compounds, for example with hydrogen peroxide, it is possible to obtain the corresponding sulfoxides (II, m=1) or sulfones (II, m=2).

Another way of preparing those aniline derivatives of the formula II where m is 2 comprises for example reacting a sulfinate of the formula X

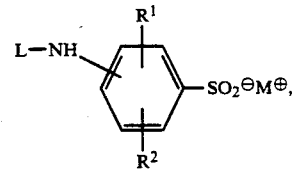
(X)

where $R^1$ and $R^2$ are each as defined above, L is $C_1$-$C_4$-alkanoyl and $M^\oplus$ is an alkali metal cation, with the chlorobenzene derivative IX to form a sulfone of the formula XI

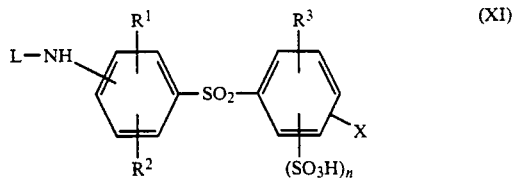
(XI)

where L, $R^1$, $R^2$, $R^3$, X and n are each as defined above. By hydrolytic elimination of the protective group L it is then possible to arrive at the target product of the formula I (where m =2). In some cases, the hydrolytic elimination of the protective group L already takes place during the formation of the sulfone; that is, the sulfone XI is not intermediately isolated.

The sulfinates X are obtainable for example by reduction from the corresponding sulfonyl chlorides.

The components of the formulae VII, VIII, IX and X are in general compounds known per se.

In what follows, some aniline derivatives of the formula II and suitable aminophenol derivatives of the formula III are given as examples.

Aniline derivatives of the formula II are for example:

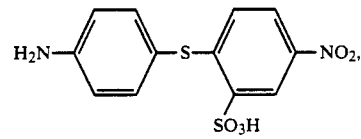

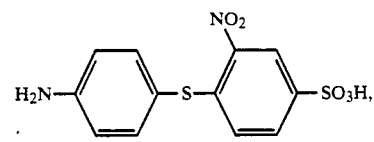

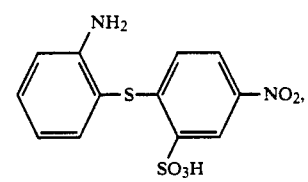

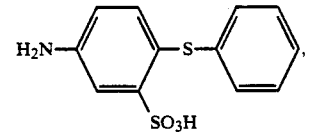

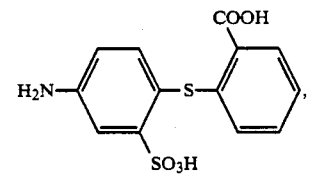

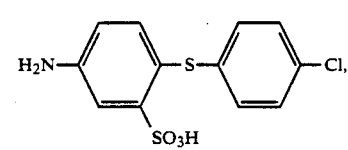

-continued
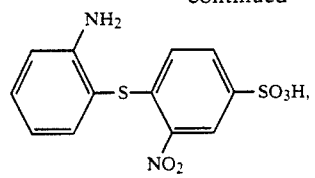
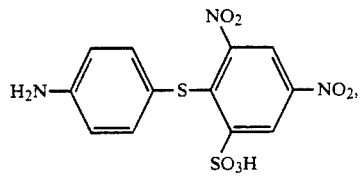
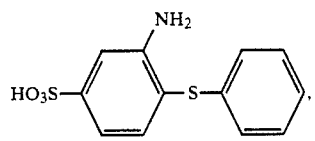
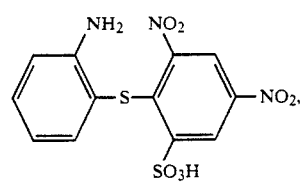
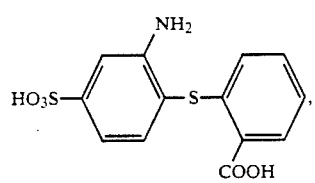
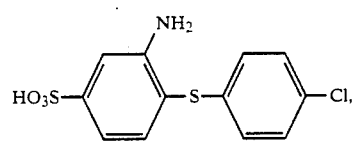
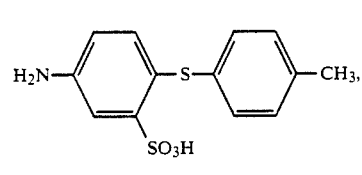
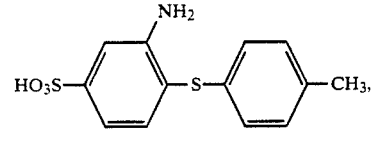
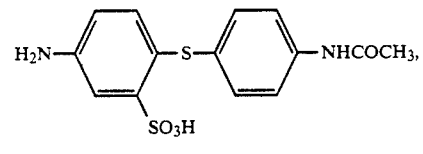
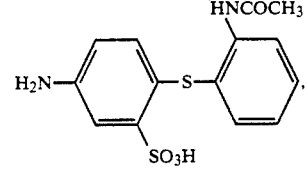
-continued
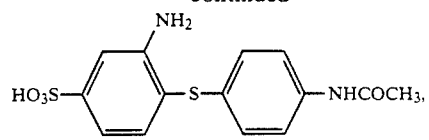
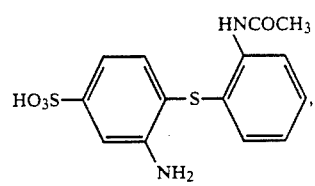
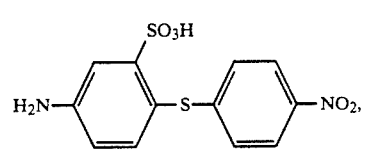
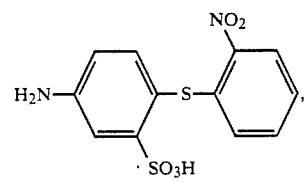
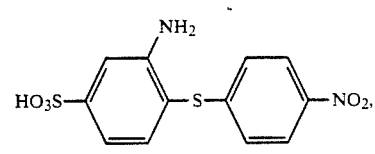
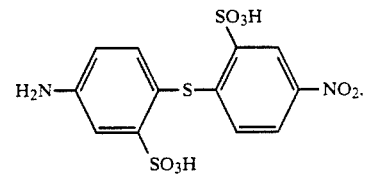
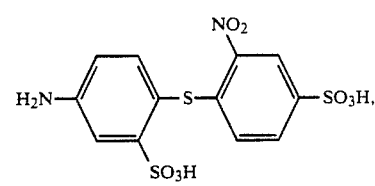
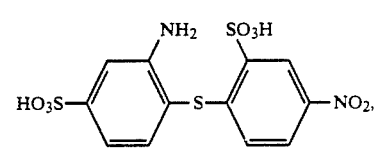
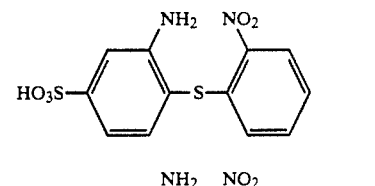
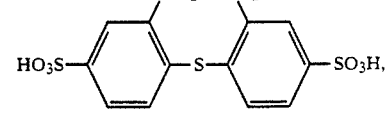

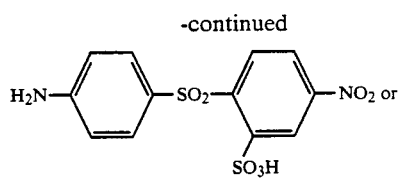

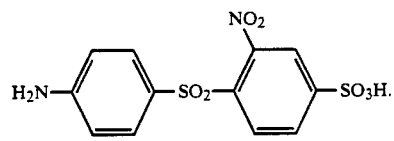

Aminophenols of the formula III are for example:

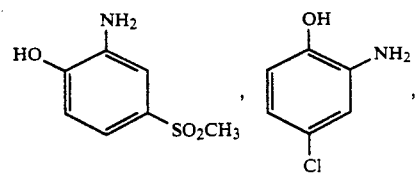

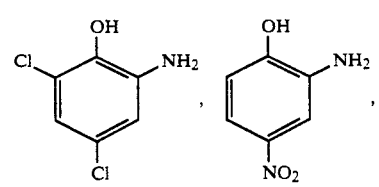

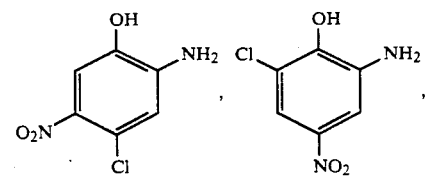

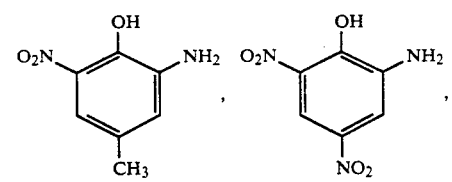

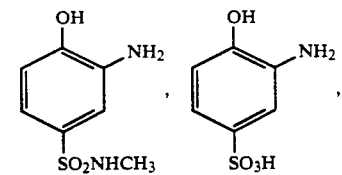

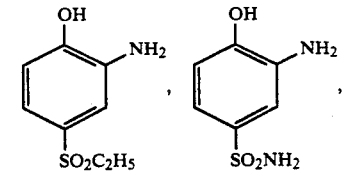

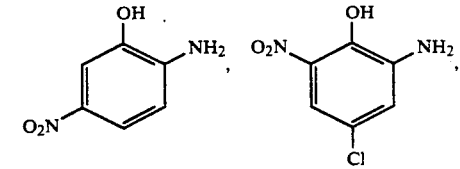

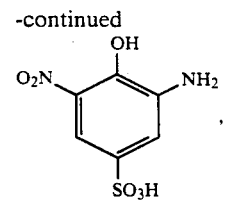

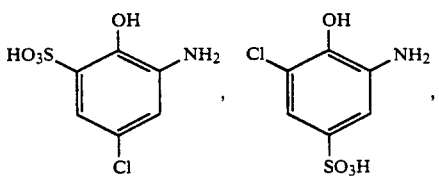

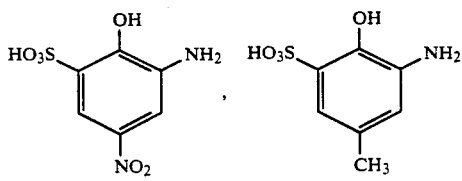

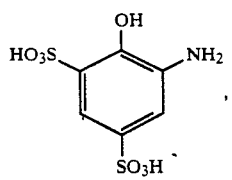

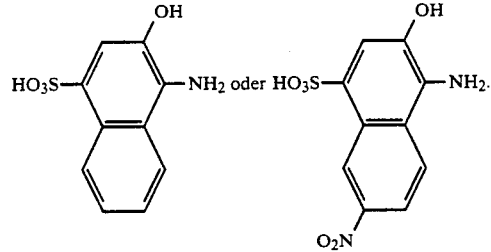

The polyazo dyes according to the invention are suitable in an advantageous manner for dyeing leather.

The Examples which follow will illustrate the invention in more detail. The percentages are by weight.

EXAMPLE 1

19.9 g of 1-amino-2-hydroxy-3,5-dinitrobenzene were conventionally diazotized and coupled onto 11 g of resorcinol under alkaline conditions. To the suspension at pH 8-9 was then added the diazonium salt of 32.6 g of 4-amino-4'-nitro-2'-sulfodiphenyl sulfide. After the coupling had ended, the reaction mixture was adjusted with acidic acid to pH 5, admixed with 38 g of anhydrous iron(III) chloride and heated at pH 4-5 and 90°-95° C. for about 3 hours.

After the metallization had taken place, the dye was precipitated by adding sodium chloride, isolated and dried. The iron complex of the compound of the formula

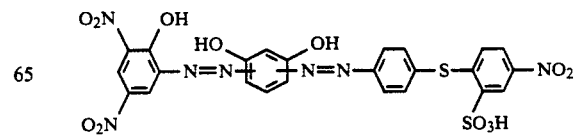

dyes leather in light- and wet-fast yellowish brown shades.

The dyes listed in the Table below are prepared in a similar manner.

TABLE 1

A—N=N—[resorcinol core with HO and OH]—N=N—R

| Ex. | A | R | Shade of dyeing of metal complexes on leather | | | | |
|---|---|---|---|---|---|---|---|
| | | | Cu | Cr | Co | Ni | Fe |
| 2 | 2,4-dinitro-6-hydroxyphenyl (O$_2$N, OH, O$_2$N) | –C$_6$H$_4$–S–C$_6$H$_3$(NO$_2$)(SO$_3$H) | reddish brown | | | reddish brown | |
| 3 | 2,4-dinitro-6-hydroxyphenyl | –C$_6$H$_4$–S–C$_6$H$_3$(NO$_2$)(SO$_3$H) | | reddish brown | | | yellowish brown |
| 4 | 2-chloro-4-nitro-6-hydroxyphenyl | –C$_6$H$_4$–SO$_2$–C$_6$H$_3$(NO$_2$)(SO$_3$H) | brown | | | reddish brown | yellowish brown |
| 5 | 2-chloro-4-nitro-6-hydroxyphenyl | –C$_6$H$_4$–S–C$_6$H$_3$(NO$_2$)(SO$_3$H) | reddish brown | brown | | | yellowish brown |
| 6 | 2,4-dichloro-6-hydroxyphenyl | –C$_6$H$_4$–S–C$_6$H$_3$(NO$_2$)(SO$_3$H) | | brown | | | yellowish brown |
| 7 | 4-nitro-2-hydroxyphenyl | –C$_6$H$_4$–S–C$_6$H$_3$(NO$_2$)(SO$_3$H) | | | | reddish brown | yellowish brown |
| 8 | 2-nitro-4-chloro-6-hydroxyphenyl | –C$_6$H$_4$–S–C$_6$H$_3$(NO$_2$)(SO$_3$H) | | reddish brown | | | yellowish brown |

TABLE 1-continued $$A-N=N-\underset{\underset{OH}{|}}{\overset{\overset{HO}{|}}{C_6H_2}}-N=N-R$$

| Ex. | A | R | Shade of dyeing of metal complexes on leather | | | | |
|---|---|---|---|---|---|---|---|
| | | | Cu | Cr | Co | Ni | Fe |
| 9 | 4-chloro-2-hydroxyphenyl (OH, Cl) | 4-[(2-nitro-4-sulfophenyl)thio]phenyl | reddish brown | reddish brown | | | |
| 10 | 4-sulfo-2-hydroxyphenyl (OH, HO₃S) | 4-[(4-nitro-2-sulfophenyl)thio]phenyl | reddish brown | | | | yellowish brown |
| 11 | 4-sulfamoyl-2-hydroxyphenyl (OH, H₂NSO₂) | 4-[(4-nitro-2-sulfophenyl)thio]phenyl | | brown | | brown | yellowish brown |
| 12 | 4-(N,N-dimethylsulfamoyl)-2-hydroxyphenyl (OH, (CH₃)₂NSO₂) | 4-[(2-nitro-4-sulfophenyl)thio]phenyl | | | reddish brown | | yellowish brown |
| 13 | 4-(N,N-dimethylsulfamoyl)-2-hydroxyphenyl (OH, (CH₃)₂NSO₂) | 4-[(4-nitro-2-sulfophenyl)thio]phenyl | | brown | | | yellowish brown |
| 14 | 4-methylsulfonyl-2-hydroxyphenyl (OH, CH₃SO₂) | 4-[(4-nitro-2-sulfophenyl)thio]phenyl | reddish brown | reddish brown | | | yellowish brown |
| 15 | 2-hydroxy-3,5-dinitrophenyl (O₂N, OH, O₂N) | 4-[(4-nitro-2-sulfophenyl)sulfonyl]phenyl | reddish brown | reddish brown | | | yellowish brown |
| 16 | 2-hydroxy-3,5-dinitrophenyl (O₂N, OH, O₂N) | 4-[(2-sulfophenyl)thio]phenyl | reddish brown | reddish brown | | | yellowish brown |

TABLE 1-continued $$A-N{=}N-\underset{\underset{}{\text{(resorcinol core with HO, OH)}}}{}-N{=}N-R$$

| Ex. | A | R | Shade of dyeing of metal complexes on leather | | | | |
|---|---|---|---|---|---|---|---|
| | | | Cu | Cr | Co | Ni | Fe |
| 17 | 2-HO₃S-4-O₂N-6-methyl-phenol (HO₃S, OH, CH₃, O₂N substituted benzene) | 4-(2-SO₃H-4-NO₂-phenylthio)phenyl | reddish brown | | | | yellowish brown |
| 18 | 2-HO₃S-4-Cl-6-methyl-phenol | 4-(2-SO₃H-4-NO₂-phenylthio)phenyl | | reddish brown | | | yellowish brown |
| 19 | 1-HO₃S-3-OH-4-methyl-naphthyl | 4-(2-SO₃H-4-NO₂-phenylthio)phenyl | | | | reddish brown | |
| 20 | 1-HO₃S-3-OH-4-methyl-6-O₂N-naphthyl | 4-(2-SO₃H-4-NO₂-phenylthio)phenyl | reddish brown | | | | brown |
| 21 | 2-HO₃S-4-CH₃-6-methyl-phenol | 4-(2-NO₂-4-SO₃H-phenylthio)phenyl | reddish brown | | | | brown |
| 22 | 2,4-di-HO₃S-6-methyl-phenol | 4-(4-Cl-2-SO₃H-phenylthio)phenyl | | | reddish brown | | brown |
| 23 | 2,4-di-O₂N-6-methyl-phenol | 2-SO₃H-4-NO₂-phenyl-(phenylthio) | reddish brown | | | | yellowish brown |

TABLE 1-continued $$\text{A}-\text{N}=\text{N}-\underset{\underset{\text{OH}}{|}}{\overset{\overset{\text{HO}}{|}}{\bigcirc}}-\text{N}=\text{N}-\text{R}$$

| | | | Shade of dyeing of metal complexes on leather | | | | |
|---|---|---|---|---|---|---|---|
| Ex. | A | R | Cu | Cr | Co | Ni | Fe |
| 24 | 2-Cl, 4-NO₂, 6-OH phenyl | 2-SO₃H, 4-NO₂ phenyl — S — (2-methylphenyl) | | reddish brown | | | yellowish brown |
| 25 | 2,4-(O₂N)₂, 6-OH phenyl | 2-COOH phenyl — S — (4-SO₃H phenyl) | reddish brown | | | reddish brown | |
| 26 | 2,4-(O₂N)₂, 6-OH phenyl | 4-NHCOCH₃ phenyl — S — (4-SO₃H phenyl) | | reddish brown | | | yellowish brown |
| 27 | 2-OH, 4-H₂NSO₂ phenyl | 2-NO₂, 4-NO₂, 6-SO₃H phenyl — S — phenyl | | reddish brown | | | yellowish brown |
| 28 | 2-OH, 4-(CH₃)₂NSO₂ phenyl | 2-SO₃H, 4-NO₂ phenyl — S — (2-methylphenyl) | | reddish brown | | | yellowish brown |

TABLE 2

$$\text{A}-\text{N}=\text{N}-\underset{\underset{\text{NH}_2}{|}}{\overset{\overset{\text{HO}}{|}}{\bigcirc}}-\text{N}=\text{N}-\text{R}$$

| | | | Shade of dyeing of metal complexes on leather | | | | |
|---|---|---|---|---|---|---|---|
| Ex. | A | R | Cu | Cr | Co | Ni | Fe |
| 29 | 2-O₂N, 4-O₂N, 6-OH phenyl | 4-NO₂, 2-SO₃H phenyl — S — phenyl | reddish brown | | | | yellowish brown |

TABLE 2-continued $$A-N=N-\underset{\substack{HO \\ \phantom{A}}}{\bigcirc}-N=N-R$$

(with HO and NH₂ substituents on the central ring)

| Ex. | A | R | Shade of dyeing of metal complexes on leather | | | | |
|---|---|---|---|---|---|---|---|
| | | | Cu | Cr | Co | Ni | Fe |
| 30 | 2-hydroxy-3,5-dinitrophenyl (O₂N, OH, O₂N) | 3-nitro-4-(4-sulfophenylthio)phenyl (NO₂, S-C₆H₄-SO₃H) | | reddish brown | | | yellowish brown |
| 31 | 3-chloro-2-hydroxy-5-nitrophenyl (Cl, OH, O₂N) | 4-nitro-2-sulfo-phenyl(4-thio)phenyl (NO₂, SO₃H, S) | | reddish brown | | | reddish brown |
| 32 | 2-hydroxy-5-nitrophenyl (OH, O₂N) | 4-nitro-2-sulfo-phenyl(4-thio)phenyl | reddish brown | reddish brown | | | brown |
| 33 | 2-hydroxy-5-sulfamoylphenyl (OH, H₂NSO₂) | 3-nitro-4-(4-sulfophenylthio)phenyl | | reddish brown | | | reddish brown |
| 34 | 3-chloro-2-hydroxy-5-sulfophenyl (Cl, OH, HO₃S) | 4-nitro-2-sulfo-phenyl(4-thio)phenyl | | reddish brown | | | brown |
| 35 | 2-hydroxy-3-sulfo-5-nitrophenyl (HO₃S, OH, O₂N) | 4-nitro-2-sulfo-phenyl(4-thio)phenyl | reddish brown | reddish brown | | | |
| 36 | 2-hydroxy-3-sulfo-5-methylphenyl (HO₃S, OH, CH₃) | 4-nitro-2-sulfo-phenyl(4-thio)phenyl | | reddish brown | | | brown |
| 37 | 2-hydroxy-3,5-dinitrophenyl (O₂N, OH, O₂N) | 2-sulfo-4-(phenylthio)phenyl (SO₃H, S-C₆H₅) | | reddish brown | | | yellowish brown |

TABLE 2-continued $$\text{A—N}=\text{N}-\overset{\overset{\displaystyle HO}{|}}{\underset{\underset{\displaystyle N=N-R}{|}}{\bigcirc}}-\text{NH}_2$$

| | | | Shade of dyeing of metal complexes on leather | | | | |
|---|---|---|---|---|---|---|---|
| Ex. | A | R | Cu | Cr | Co | Ni | Fe |
| 38 | 2,4-dinitro-6-hydroxyphenyl (O₂N, OH, O₂N) | phenyl-S-(4-methylphenyl) with SO₃H | | reddish brown | | | yellowish brown |
| 39 | 2-chloro-4-nitro-6-hydroxyphenyl (Cl, OH, O₂N) | (2-methylphenyl)-S-(2-SO₃H, 4-NO₂-phenyl) | reddish brown | | | reddish brown | |
| 40 | 4-sulfamoyl-2-hydroxyphenyl (OH, H₂NSO₂) | phenyl(SO₃H)-S-(2-methyl-4-chlorophenyl) | reddish brown | | | | yellowish brown |
| 41 | 4-nitro-2-hydroxyphenyl (OH, O₂N) | (2-methylphenyl)-S-(2-NO₂, 4-SO₃H-phenyl) | | reddish brown | | | yellowish brown |
| 42 | 2-hydroxy-3-sulfo-5-nitrophenyl (HO₃S, OH, O₂N) | phenyl(SO₃H)-S-(4-NHCOCH₃-phenyl) | | reddish brown | | | yellowish brown |

TABLE 3

$$\text{A—N}=\text{N}-\overset{\overset{\displaystyle H_2N}{|}}{\underset{\underset{\displaystyle N=N-R}{|}}{\bigcirc}}-\text{NH}_2$$

| | | | Shade of dyeing of metal complexes on leather | | | | |
|---|---|---|---|---|---|---|---|
| Ex. | A | R | Cu | Cr | Co | Ni | Fe |
| 43 | 2,4-dinitro-6-hydroxyphenyl (O₂N, OH, O₂N) | phenyl-S-(2-SO₃H, 4-NO₂-phenyl) | reddish brown | | | | yellowish brown |

TABLE 3-continued $$A-N=N-\underset{\underset{NH_2}{|}}{\bigcirc}-N=N-R$$
(with H₂N substituent)

| | | | Shade of dyeing of metal complexes on leather | | | | |
|---|---|---|---|---|---|---|---|
| Ex. | A | R | Cu | Cr | Co | Ni | Fe |
| 44 | 2-hydroxy-3-sulfo-5-nitrophenyl (HO₃S, OH, O₂N substituents) | 4-(4-chlorophenylthio)-3-sulfophenyl | | reddish brown | | | brown |
| 45 | 2-hydroxy-3-sulfo-5-chlorophenyl (HO₃S, OH, Cl) | 4-(2-sulfo-4-nitrophenylthio)phenyl | | | | reddish brown | |
| 46 | 2-hydroxy-5-nitrophenyl (OH, O₂N) | 4-(2-sulfo-4-nitrophenylthio)phenyl | reddish brown | | | | |
| 47 | 2-hydroxy-5-sulfamoylphenyl (OH, H₂NSO₂) | 4-(2-sulfo-4-nitrophenylthio)phenyl | | brown | | | yellowish brown |
| 48 | 2-hydroxy-3-chloro-5-nitrophenyl (Cl, OH, O₂N) | 4-(2-nitro-4-sulfophenylthio)phenyl | | reddish brown | | | yellowish brown |
| 49 | 2-hydroxy-3-methyl-5-nitrophenyl (H₃C, OH, O₂N) | 4-(2-sulfo-4-nitrophenylthio)phenyl | | reddish brown | | | reddish brown |
| 50 | 2-hydroxy-5-methylsulfonylphenyl (OH, CH₃SO₂) | 4-(2-sulfo-4-nitrophenylthio)phenyl | | reddish brown | | | yellowish brown |
| 51 | 4-(4-nitro-2-sulfophenylthio)phenyl (O₂N, HO₃S) | 2-hydroxy-3,5-dinitrophenyl (HO, NO₂, NO₂) | | reddish brown | reddish brown | | yellowish brown |

TABLE 3-continued $$A-N=N-\underset{\underset{NH_2}{|}}{\overset{\overset{H_2N}{|}}{C_6H_2}}-N=N-R$$

| | | | Shade of dyeing of metal complexes on leather | | | | |
|---|---|---|---|---|---|---|---|
| Ex. | A | R | Cu | Cr | Co | Ni | Fe |
| 52 | 2,4-dinitro-phenol (O₂N, OH, O₂N) | 4-nitro-2-(phenylthio)benzenesulfonic acid | | reddish brown | | | yellowish brown |
| 53 | 4-sulfamoyl-phenol (OH, H₂NSO₂) | 2-nitro-4-sulfo-(o-tolylthio)benzene | reddish brown | | | reddish brown | yellowish brown |
| 54 | 3-nitro-4-hydroxy-benzenesulfonic acid (O₂N, OH, HO₃S) | 4-(4-nitro-2-sulfophenylthio)phenyl | | reddish brown | | | yellowish brown |
| 55 | 2,4-dinitrophenol-sulfonic (O₂N, OH, O₂N) | 2-(4-chlorophenylthio)-benzenesulfonic acid | | reddish brown | | | yellowish brown |
| 56 | 4-hydroxybenzenesulfonic acid (OH, HO₃S) | 4-(2-nitro-4-sulfo-phenylthio)phenyl | | reddish brown | | | brown |

EXAMPLE 57

19.9 g of 1-amino-2-hydroxy-3,5-dinitrobenzene were conventionally diazotized and coupled onto 11 g of resorcinol under alkaline conditions. To the suspension was then added at pH 8-9 the diazonium salt of 32.6 g of 4-amino-4'-nitro-2'-sulfodiphenyl sulfide. After the disazo dye had been formed, the diazocompound of 21.8 g of 1-amino-4-nitrobenzene-2-sulfonic acid was added in such a way that the coupling took place at pH 6-7. After the coupling had ended, the reaction mixture was adjusted with acetic acid to pH 5 and complexed with anhydrous iron(III) chloride as described in Example 1.

After the metallization had taken place, the dye was precipitated by addition of sodium chloride, isolated and dried. The iron complex of the compound of the formula

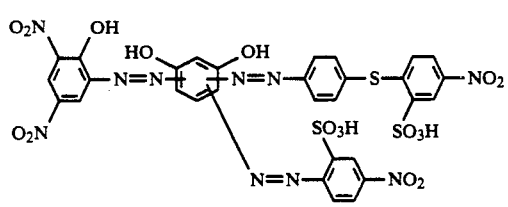

dyes vegetable/synthetically retanned chrome leather in light- and wet-fast brown shades.

The dyes listed in the Table below are obtained in a similar manner.

TABLE 4

Structure: (O₂N)₂(OH)C₆H₂—N=N—[C₆H₂(OH)₂(N=N-X)]—N=N—R (trisazo dye with picric-acid-type left ring and resorcinol-type central ring bearing two azo groups to R and X)

| Ex. | R | X | Shade of Fe complex on leather |
|-----|---|---|-------------------------------|
| 58 | 4-(4-nitro-2-sulfophenylthio)phenyl | 4-chlorophenyl | yellowish brown |
| 59 | 4-(4-nitro-2-sulfophenylthio)phenyl | 4-nitrophenyl | brown |
| 60 | 4-(2-nitro-4-sulfophenylthio)phenyl | 3-nitro-4-sulfophenyl | yellowish brown |
| 61 | 4-(4-nitro-2-sulfophenylthio)phenyl | 6-sulfonaphth-2-yl | brown |
| 62 | 4-(phenylthio)-3-sulfophenyl | 2-nitro-4-sulfophenyl | reddish brown |
| 63 | 4-(4-methylphenylthio)-3-sulfophenyl | 4-chloro-3-sulfophenyl | brown |
| 64 | 4-(4-nitro-2-sulfophenylsulfonyl)phenyl | 3-sulfo-4-nitrophenyl | brown |
| 65 | 4-(4-nitro-2-sulfophenylthio)phenyl | 4-sulfophenyl | brown |

TABLE 4-continued

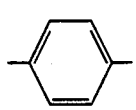

| Ex. | R | X | Shade of Fe complex on leather |
|---|---|---|---|
| 66 | 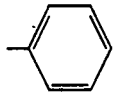 | 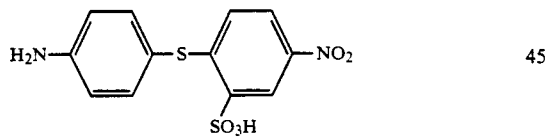 | brown |

EXAMPLE 67

81 g of 60% strength sodium sulfide, dissolved in 200 ml of water, were added dropwise with stirring to a hot melt at 90° C. of 39.5 g of 4-nitrochlorobenzene in 250 ml of water in the course of about 15 minutes, during which the reaction mixture came to the boil. After two hours at an unchanged temperature, the solution of 4-aminothiophenol was cooled down to room temperature, diluted with 350 ml of water and adjusted with about 26 ml of acetic acid from pH 12 to pH 8. 59.5 g of 4-nitrochlorobenzene-2-sulfonic acid were then added. After five hours' stirring at 80° C., the solution was cooled down to 60° C., and the resulting product was precipitated at pH 1 with dilute hydrochloric acid and filtered off with suction. For purification, the filtered residue was dissolved at 80° C. in 400 ml with dilute sodium hydroxide solution at pH 12, filtered, precipitated as described above, filtered off with suction and then washed until salt-free and neutral. Drying at 80° C. under reduced pressure left 70 g of 4-amino-4'-nitro-2'-sulfodiphenyl sulfide of the formula

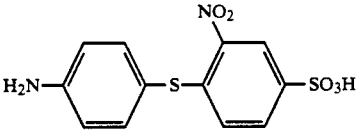

(corresponding to about 86% of theory, based on starting 4-nitrochlorobenzene).

The aniline derivatives listed in Table 5 below are obtained in a similar manner.

TABLE 5

| Compound No. | |
|---|---|
| 68 | 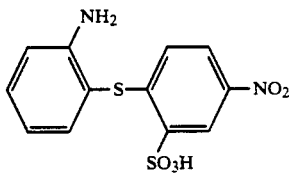 |
| 69 | 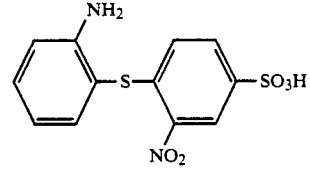 |
| 70 | 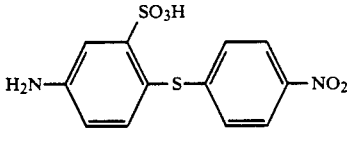 |
| 71 | 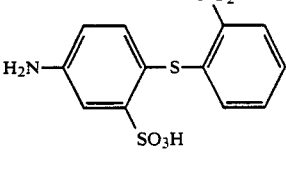 |
| 72 | 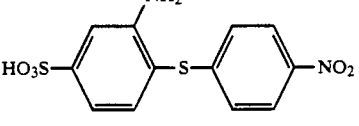 |
| 73 | 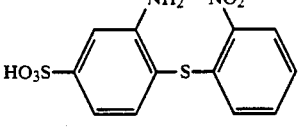 |
| 74 | 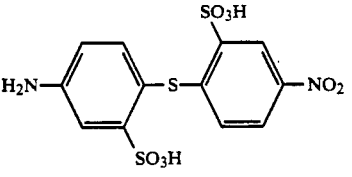 |
| 75 | 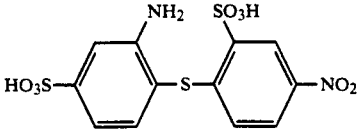 |
| 76 |  |

TABLE 5-continued

| Compound No. | |
|---|---|
| 77 | 4-H₂N-C₆H₃(SO₃H)-S-C₆H₃(NO₂)-SO₃H |
| 78 | HO₃S-C₆H₃(NH₂)-S-C₆H₃(NO₂)-SO₃H |
| 79 | H₂N-C₆H₄-S-C₆H₂(NO₂)₂(SO₃H) |
| 80 | C₆H₄(NH₂)-S-C₆H₂(NO₂)₂(SO₃H) |

EXAMPLE 81

55 g of thiophenol and 250 g of 4-nitrochlorobenzene-2-sulfonic acid were introduced into 1000 ml of water with stirring. The reaction mixture was then brought to pH 11 with dilute sodium hydroxide solution, which raised the temperature exothermically to 55° C. The batch was then stirred at 50° C. for two hours and thereafter at 80° C. for a further two hours, admixed with 100 g of sodium chloride, cooled to room temperature amd filtered with suction. The filter cake was then introduced a little at a time at 85°–90° C. into a reduction mixture prepared from 200 g of iron powder, 600 ml of water and 150 ml of 5N hydrochloric acid. The reduction was complete after one hour at 90° C. After the pH had been raised to 10-11 with dilute sodium hydroxide solution, the iron sludge was filtered off hot and thoroughly washed with hot water, and the filtrate was acidified at room temperature with dilute hydrochloric acid. The precipitate of the aniline derivative was filtered off with suction and washed with cold water until neutral. Drying under reduced pressure at 80° C. left 121 g of 4-amino-2-sulfodiphenyl sulfide of the formula

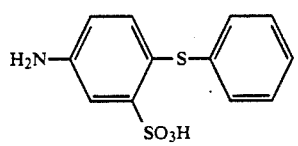

(corresponding to about 84% of theory, based on starting thiophenol).

The aniline derivatives listed in Table 6 below are obtained in a similar manner.

TABLE 6

| Compound No. | |
|---|---|
| 82 | H₂N-C₆H₄-S-C₆H₄-COOH (SO₃H) |
| 83 | H₂N-C₆H₃(SO₃H)-S-C₆H₄-Cl |
| 84 | HO₃S-C₆H₃(NH₂)-S-C₆H₅ |
| 85 | HO₃S-C₆H₃(NH₂)-S-C₆H₄-Cl |
| 86 | HO₃S-C₆H₃(NH₂)-S-C₆H₄-COOH |
| 87 | H₂N-C₆H₃(SO₃H)-S-C₆H₄-CH₃ |
| 88 | HO₂S-C₆H₃(NH₂)-S-C₆H₄-CH₃ |

EXAMPLE 89

32.6 g of 4-amino-4'-nitro-2'-sulfodiphenyl sulfide were dissolved in 300 ml of water by stirring with dilute sodium hydroxide solution at pH 8–9, and 15 g of sodium carbonate were added, followed dropwise at 50° C. by 30 ml of acetic anhydride. After the acetylation had ended, the solution was heated to 90° C., and 50 g of iron powder were added a little at a time in the course of 30 minutes. After a further 30 minutes in the same temperature range, the reduction had ended, and the rest of the procedure was as in Example 81. Drying left 23 g of 4-amino-4'-acetylamino-2-sulfodiphenyl sulfide of the formula

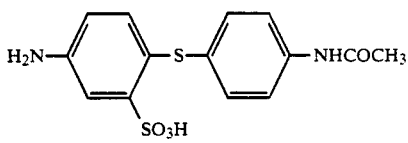

The aniline derivatives listed in Table 7 below are obtained in a similar manner.

TABLE 7

| Compound No. | |
|---|---|
| 90 | ![structure with H2N, S, NHCOCH3, SO3H] |
| 91 | ![structure with HO3S, NH2, S, NHCOCH3] |
| 92 | ![structure with HO3S, S, HNCOCH3, NH2] |

EXAMPLE 93

32.6 g of 4-amino-4'-nitro-2'-sulfodiphenyl sulfide were acetylated as described in Example 89 and, after the reaction had ended, admixed at 80° C. with 30 ml of 30% strength hydrogen peroxide in the course of one hour. After 30 minutes the oxidation product was alkali-hydrolyzed at the boil and filtered hot, and the filtrate was brough to pH 6-7 with concentrated hydrochloric acid and then evaporated to dryness under reduced pressure. To separate off inorganic salts, the residue was decocted with methanol, and the filtrate was again evaporated under reduced pressure. The residue of crude 4-amino-4'-nitro-2,-sulfodiphenyl sulfone (Na salt) of the formula

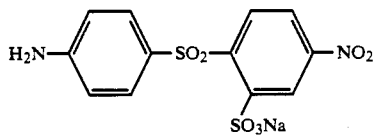

was taken up in acetone, stirred, filtered off with suction and dried (yield: 33 g).

EXAMPLE 94

730 ml of water and 159 g of $Na_2SO_3$ (95% strength by weight) were introduced first. 530 g of 4-acetylaminobenzenesulfonyl chloride were then added a little at a time with stirring at 70° C., while the pH was maintained at about 9 with 95 ml of 50% strength by weight sodium hydroxide solution. After 3 hours of subsequent stirring at 70° C., insolubles were filtered off, 250 g of ice were added at 30° C., and 375 ml of 17% strength by weight hydrochloric acid were added with stirring at pH 1.0 to bring down a precipitate, while the temperature was maintained at ≦10° C. The resulting suspension was filtered with suction after 1.5 hours and the filter residue was washed with 1.5 l of ice-water. The filter material was then suspended in 400 ml of ice-water and dissolved at about 15° C. with 74 ml of 30% strength by weight sodium hydroxide solution at pH 9.0. This gave 782 ml of a clear solution containing 185 g of the sodium salt of 4-acetylaminobenzenesulfinic acid.

654 ml of this solution (corresponding to 154.7 g of the sodium salt of 4-acetylaminobenzenesulfinic acid) were introduced first, and 365 g of 50% strength by weight 2-nitrochlorobenzene-4-sulfonic acid were added with stirring at pH 6.2. The pH was then adjusted to 7.0 with a few drops of sodium hydroxide solution. 9 g of $CaCO_3$ and 0.35 g of copper powder were added, and the mixture was stirred at 100° C. for 20 hours and then filtered hot.

The resulting solution was admixed with 180 ml of 17% strength by weight hydrochloric acid and refluxed for 4 hours. The suspension obtained was then filtered with suction at room temperature, and the filter residue was washed with 2 l of ice-water and dried at 70° C. under reduced pressure. Yield: 250 g of 4-amino-2'-nitro-4'-sulfodiphenyl sulfone of the formula

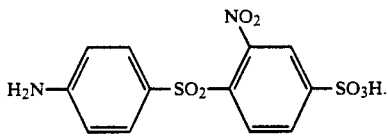

We claim:
1. A polyazo of the formula I

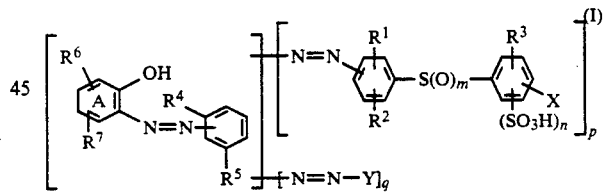

where
m is 0 or 2,
n is 1,
p is from 1 to 2,
q is from 0 to 1,
X is nitro,
$R^1$ and $R^2$ are identical or different and each is independently of the other hydrogen or $C_1$-$C_4$-alkoxy,
$R^3$ is hydrogen,
$R^4$ and $R^5$ are identical or different and each is independently of the other hydroxyl or amino,
$R^6$ is hydrogen, $C_1$-$C_4$-alkyl, halogen, nitro, hydroxysulfonyl, sulfamoyl, $C_1$-$C_4$-monoalkylsulfamoyl, $C_1$-$C_4$-dialkylsulfamoyl or $C_1$-$C_4$-alkylsufonyl,
$R^7$ is hydrogen, halogen, nitro or hydroxysulfonyl and
Y is a radical of the formula

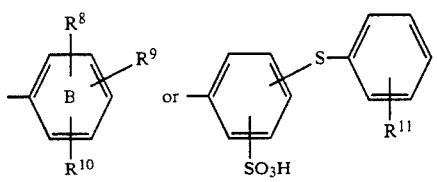

where $R^8$ is hydrogen, hydroxyl, halogen, nitro or hydroxysulfonyl, $R^9$ is hydrogen, halogen, nitro or hydroxysulfonyl, $R^{10}$ is hydrogen, $C_1$-$C_4$-alkyl, $C_1$-$C_4$-alkoxy or hydroxysulfonyl and $R^{11}$ is hydrogen, $C_1$-$C_4$-alkyl, $C_1$-$C_4$-alkoxy, halogen or carboxyl, and the ring A or unfused or fused with an unsubstituted or nitro-or hydroxysulfonyl-substituted benzo ring, in the free form or as a copper, chromium, iron, cobalt or nickel complex.

2. A polyazo dye as claimed in claim 1, wherein, m is 0, q is 0, and $R^1$ and $R^2$ are each hydrogen.

* * * * *